(12) United States Patent
Akaishi et al.

(10) Patent No.: US 7,980,778 B2
(45) Date of Patent: Jul. 19, 2011

(54) LIQUID APPLICATOR

(75) Inventors: Tetsuaki Akaishi, Fujioka (JP); Takashi Umeno, Fujioka (JP); Mitsuru Endoh, Fujioka (JP); Nobuyuki Nakajima, Fujioka (JP)

(73) Assignee: Mitsubishi Pencil Co., Ltd., Shinagawa-Ku, Tokyo (JP)

( * ) Notice: Subject to any disclaimer, the term of this patent is extended or adjusted under 35 U.S.C. 154(b) by 978 days.

(21) Appl. No.: 11/665,677

(22) PCT Filed: Nov. 7, 2005

(86) PCT No.: PCT/JP2005/020383
§ 371 (c)(1),
(2), (4) Date: Apr. 18, 2007

(87) PCT Pub. No.: WO2006/049283
PCT Pub. Date: May 11, 2006

(65) Prior Publication Data
US 2009/0038545 A1 Feb. 12, 2009

(30) Foreign Application Priority Data
Nov. 8, 2004 (JP) .................. 2004-323749

(51) Int. Cl.
*B05C 11/00* (2006.01)
(52) U.S. Cl. .................. 401/266; 401/263; 401/264
(58) Field of Classification Search .......... 401/263–267, 401/186, 171–175
See application file for complete search history.

(56) References Cited

U.S. PATENT DOCUMENTS

| | | | |
|---|---|---|---|
| 2,442,503 A | 6/1948 | Melnikoff | |
| 3,032,803 A | 5/1962 | Walshauser | |
| 4,693,623 A | 9/1987 | Schwartzman | |
| 5,772,347 A * | 6/1998 | Gueret | .......... 401/263 |
| 5,803,640 A | 9/1998 | Nakajima et al. | |
| 5,879,095 A | 3/1999 | Gueret | |
| 5,879,096 A * | 3/1999 | Franta et al. | .......... 401/175 |
| 5,961,007 A * | 10/1999 | Dornbusch et al. | .......... 222/386 |
| 6,305,863 B1 | 10/2001 | Gueret | |
| 6,918,515 B2 | 7/2005 | Noguchi | |
| 2002/0014254 A1 | 2/2002 | Gueret | |
| 2004/0005185 A1 | 1/2004 | Endo | |
| 2004/0042841 A1 | 3/2004 | Noguchi | |

FOREIGN PATENT DOCUMENTS

| | | |
|---|---|---|
| DE | 4016353 A1 | 5/1990 |
| EP | 0715820 A2 | 6/1996 |
| EP | 0715820 A3 | 6/1996 |

(Continued)

*Primary Examiner* — David J Walczak
(74) *Attorney, Agent, or Firm* — Buchanan Ingersoll & Rooney PC

(57) ABSTRACT

A liquid applicator includes a liquid pressing mechanism 6 for pressurizing an application liquid 4 inside a main body 2 so as to supply the application liquid to an applying member 10 at the front end by the pressing of liquid pressing mechanism 6, wherein the applying member 10 is made of an elastic material, has a valve structure 8 which is formed with a communication path 24 for communication between the inside and outside of main body 2 and can close the communication path 24 by elasticity in the normal condition and open the communication path 24 by elastic deformation of the communication path when the application liquid is pressurized by liquid pressing mechanism 6, and, an ejection opening 24a of communication path 24 of valve structure 8 is arranged to front onto the applying portion 10a of the applying member 10.

12 Claims, 11 Drawing Sheets

FOREIGN PATENT DOCUMENTS

| | | |
|---|---|---|
| EP | 1029799 A1 | 8/2000 |
| GB | 2203031 A | 10/1988 |
| JP | 63-144883 A | 9/1988 |
| JP | 08-229462 A | 9/1996 |
| JP | 09-192581 A | 7/1997 |
| JP | 09-322819 A | 12/1997 |
| JP | 2002-34648 A | 2/2002 |
| JP | 2004-89592 A | 3/2004 |

* cited by examiner

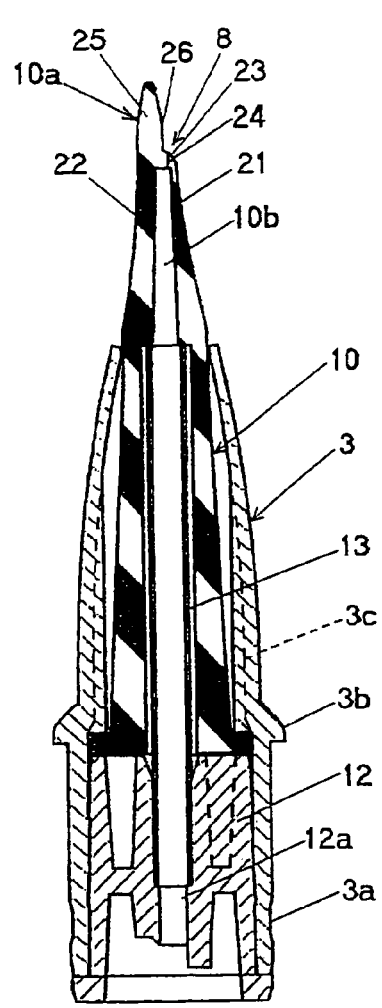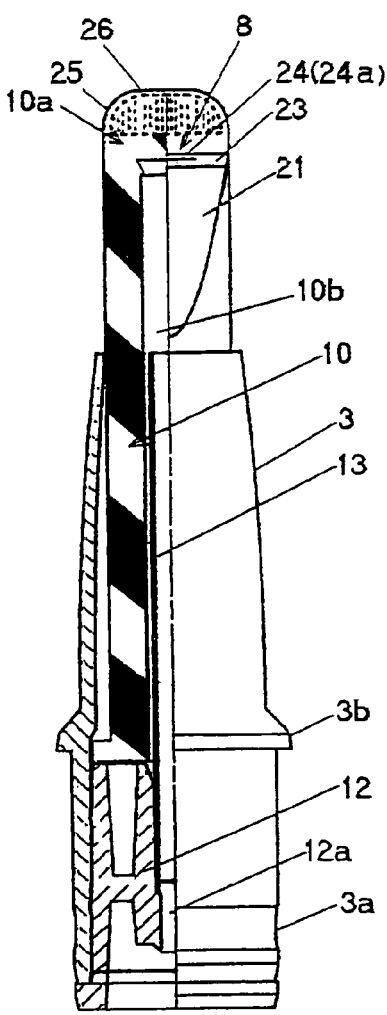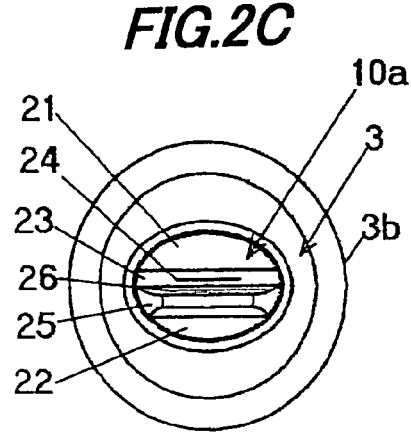

Sectional view of an inner sleeve member

Perspective view of an inner sleeve member

LIQUID APPLICATOR

TECHNICAL FIELD

The present invention relates to a liquid applicator, in particular, relating to a liquid applicator for applying an application liquid to a soft applied object such as skin, oral cavity etc.

BACKGROUND ART

Conventionally, there have been liquid applicators having a liquid pressing mechanism or liquid pressing means for pressurizing the application liquid inside the main body in order to supply the applying part with the application liquid in a timely manner.

For example, there is a proposal (see Patent document 1) of a liquid applicator that includes: an applying member attached at the front end of its barrel cylinder; a tank arranged inside the barrel for reserving a liquid in the rear of the applying member; a conduit hole portion for leading the liquid ejected from the tank to the applying member; and a liquid pushing means (liquid pressing mechanism) for pushing out the liquid inside the aforementioned tank to the applying member through the conduit hole portion by advancing a piston that is fitted in the tank so as to be slidable in its axial direction.

Also there is a proposal for a liquid container including a main body having a tank portion holding a liquid therein; a feed mechanism having a front-end feeder joined at the front end of the main body for feeding the liquid; and an actuating mechanism for pushing the liquid inside the tank portion toward the feed mechanism (see Patent document 2).

Since in the liquid applicators as above, their brush-like applying member after usage holds a considerable amount of application liquid therein and is exposed to the outside air, there is the problem that the application liquid contained in the applying member degrades with time and is liable to be decayed.

There is also a known configuration of a liquid applicator or liquid container having a mechanism for preventing against degradation of the application liquid with the passage of time or entrance of the outside air by using an elastic member.

For example, there is a proposal of an application container which includes: an application container body for storing an application liquid therein; and an applying member disposed at the front end of the application container body, for applying the application liquid over an applied object and is used to apply the application liquid to the soft applied object by bringing the front end of the applying member into contact with the applied object, wherein the applying member is made of an approximately tubular elastic body with its front and rear ends open all the time and leads the application liquid in the application container body and ejects it from the front-end opening (e.g., see Patent document 3).

However, these liquid applicators are suitable for dripping the application liquid but have the problem that it is difficult to apply the application liquid over a wide area in a simple manner. Furthermore, there is a drawback that, due to configuration of the container, it is difficult to be used in combination with a high viscous application liquid.

Patent Document 1:
Japanese Patent Application Laid-open Hei 9-322819
Patent Document 2:
Japanese Patent Application Laid-open 2004-89592
Patent Document 3:
Japanese Patent Application Laid-open Hei 9-192581

DISCLOSURE OF INVENTION

Problems to be Solved by the Invention

In view of the above conventional problems and the like, it is therefore an object of the present invention to solve the problems as well as to provide a liquid applicator which enables easy application of an application liquid even if it has high viscosity and which can protect the application liquid held therein against contamination by microbes etc. from the external air and the outside.

Means for Solving the Problems

The present inventors hereof have completed the present invention by focusing on the fact that use of an elastic material for an applying member is preferable to apply a liquid over a soft applied object and have found that the above objects can be simply achieved in combination with a liquid pressing mechanism provided for the main body by the capability of easily forming a valve structure by forming a slit hole and the like in the applying member itself taking advantage of the elasticity of the applying member, and furthermore by arranging applying portion of the applying member at the front end of the ejection opening of the valve structure.

Specifically, the liquid applicator of the present invention is characterized by any of the following configurations and means (1) to (5).

(1) A liquid applicator comprising: a liquid pressing means for pressurizing an application liquid inside a main body so as to supply the application liquid to an applying member at the front end by the pressing of the liquid pressing mechanism, characterized in that the applying member is made of an elastic material and includes: a valve structure which is formed with a communication path for communication between the inside and outside of the main body and can close the communication path by elasticity in the normal condition and open the communication path by elastic deformation of the communication path when the application liquid is pressurized by the liquid pressing means, and, an ejection opening of the communication path of the valve structure is arranged to front onto the applying portion of the applying member.

(2) The liquid applicator according to the above (1), wherein the applying portion of the applying member is formed projected further forward from the ejection opening of the communication path of the valve structure.

(3) The liquid applicator according to the above (2), wherein the applying portion projected from the ejection opening of the valve structure constitutes a liquid retainer for temporarily retaining the application liquid or includes the liquid retainer.

(4) The liquid applicator according to any one of the above (1) through (3), further comprising: a liquid depressurizing means for depressurizing the application liquid inside the main body, wherein the valve structure is configured so that, after the liquid pressing means stops pressurizing the application liquid, the valve structure can forcibly return the elastic deformation of the communication path to the normal condition by reducing the pressure on the application liquid by the liquid depressurizing means and thereby close the communication path.

(5) The liquid applicator according to the above (4), wherein the liquid pressing means and liquid depressurizing means comprise: a pressure applicator which moves forwards and backwards in the application liquid storage space inside the main body to pressurize and depressurize the application liquid; and an action converter for converting the user's rotational control over a rotary actuator which fronts on the outside of the main body, into the forward and backward movement of the pressure applicator.

(6) The liquid applicator according to the above (1), wherein the material of the elastic body used for the applying member is rubber.

(7) The liquid applicator according to the above (1), wherein the material of the elastic body used for the applying member is elastomer.

(8) The liquid applicator according to the above (1), wherein the material of the elastic body used for the applying member is a closed cellular material having resilience.

Effect of the Invention

According to the above configurations or means of the present invention, the applying member is formed of elastic material, the elastic material is formed with a communication path, and the communication path forms one that has an essentially slit-like portion being closed by its own elastic force in the normal condition.

Then, when the application liquid in the main body is pressurized by the liquid pressing means, the closed communication path is opened by elastic deformation under the pressure of the pressurized application liquid so that the application liquid is ejected from the ejection opening. When the pressure acting on the application liquid is released, the communication path returns to its normal condition free from deformation, and the communication path closes itself by its own elastic force.

Accordingly, the applying member made of elastic material and the communication path function as a valve structure of the application liquid.

Further, since the applying portion of the applying member fronts onto the ejection opening of the valve structure, the application liquid can be reliably delivered to the applying portion.

Also, since the valve structure closes the communication path and prevents bacteria and the like from entering in the normal condition, it is possible to prevent the application liquid present between the main body and the applying member from decaying or degrading, which would occur with conventional liquid applicators.

Further, after usage the applying part in the front end of the valve element can be easily wiped, so there is no application liquid remaining, which will adhere to the outside. Accordingly, even if the application liquid is high in viscosity, it is not only possible to apply the application liquid in an easy manner but also protect the stored application liquid appropriately without being affected by contamination by microbes etc., outside and without being contaminated at all by microbes and the like from the external air and the outside.

Since in the present invention the applying portion of the applying member is formed to be further projected forwards from the ejection opening of communication path of the valve structure, the application liquid delivered from the ejection opening is reliably transferred to the applying part formed at the front end and is used for application over a soft applied surface.

Accordingly, the application liquid can be easily applied and spread over the applied surface. Further, after usage the applying portion of the applying part can be easily wiped, thus making it possible to remove the application liquid which might adhere to the outside, in a more reliable manner.

Further, according to the present invention, provision of the liquid retainer for temporarily retaining the ejected application liquid in the applying part around the ejection opening of the above-described communication path, or formation of the applying part itself in such a configuration, makes it possible to temporarily hold the ejected application liquid in an efficient manner. This arrangement makes it possible to avoid dripping due to the liquid rushing out from the ejection opening, which will occur when the elastic tightness of the communication path is somehow enhanced in order for the aforementioned valve structure to easily return to its normal condition. Further, this increases the permissivity for the pressurizing operation of the liquid pressing means. Also, after usage the application liquid puddled in this liquid retainer can be wiped with tissue, rag or the like, hence it is hygienically excellent.

Further, in the present invention a liquid depressurizing means for reducing the pressure on the application liquid inside the main body is provided, and the valve structure is configured so that, after the liquid pressing means stops pressurizing the application liquid, the elastic deformation of the communication path is forcibly returned to the normal condition by reducing the pressure on the application liquid by the liquid depressurizing means to thereby close the communication path. As a result, it is possible to intentionally pull the application liquid from the communication path to the main body side and intentionally close the communication path in a reliable manner.

Accordingly, even if the application liquid being stored is viscous or high in viscosity and has such a viscosity as the application liquid will remain on the ejection side of the communication path when the liquid has been depressurized after use, it is possible to close the communication path by forcibly returning the elastic deformation of the communication path to its normal condition, by forcibly pulling the application liquid from the communication path by depressurizing the application liquid using the liquid depressurizing means.

As a result, after usage of the liquid applicator no application liquid will be present outside the ejection opening of the communication path and the communication path can be completely closed. Accordingly, regardless of whether the application liquid is high or low in viscosity, it is possible to completely eliminate the occasions of the application liquid being exposed to the outside air, being affected by contamination by microbes etc., outside and being contaminated at all by microbes and the like from the external air and the outside and to appropriately and definitely protect the stored application liquid.

In addition, since the liquid pressing means and liquid depressurizing means have a pressure applicator which moves forwards and backwards in the application liquid storage space inside the main body to pressurize and depressurize the application liquid and an action converter for converting the user's rotational control over a rotary actuator which fronts on the outside of the main body, into the forward and backward movement of the pressure applicator, it is possible to provide an integrated and simplified structure of the liquid pressing means and liquid depressurizing means.

Moreover, the action converter is formed of: a rotary actuator made up of an outer sleeve cap and an inner sleeve member which are joined so as not to be rotatable relative to each other and disposed rotatably in the main body; a holder for holding a threaded member inside the main body; and a threaded member that is engaged with the pressure applicator inside the main body and moves the aforementioned pressure applicator forwards and backwards by rotation of the inner sleeve member of the aforementioned rotary actuator, hence it is possible to achieve simplification of parts.

BRIEF DESCRIPTION OF THE DRAWINGS

FIGS. 2(a), 2(b) and 2(c) are a sectional side view of the structure of the front barrel portion of the first embodiment of a liquid applicator, its half-sectional, plan view and its view observed in the axial direction from the front end, respectively.

Figure 1:
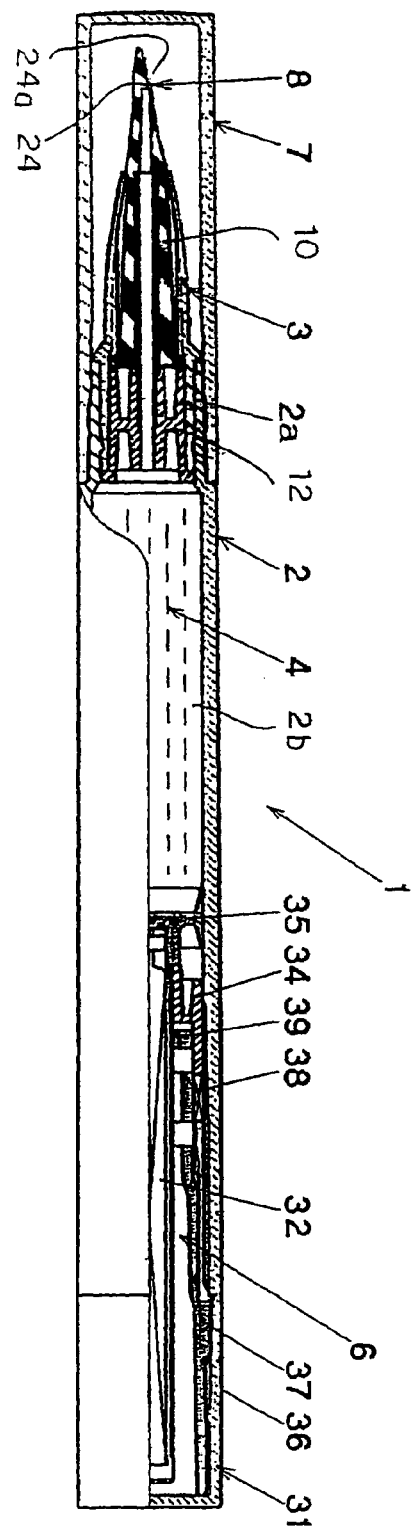
FIG. 1 is a side view according to the embodiment of a liquid applicator.

DESCRIPTION OF REFERENCE NUMERALS 1 liquid applicator
2 main body
2a small-diametric portion
2b application liquid storing space (storage tank)
3 front barrel
3a fitting recess
3b flange
3c rib
4 application liquid
6 liquid pressing mechanism (liquid pressing means)
7 cap
8 valve structure
10 applying member
10a applying portion
12 pipe joint
12a passage hole
13 application liquid feed pipe
20 liquid applicator
21 tapered portion
23 shoulder
24 communication path (slit)
24a ejection opening
25 flat portion (temporal liquid retainer)
26 roughened surface portion
31 rotary actuator
32 threaded rod
34 holder
34 large-diametric portion
34b small-diametric portion
35 piston element
36 outer sleeve cap
37 inner sleeve member
38 meshing portion
39 engaging portion
41 liquid retainer
42 acute portion
44 comb portion
45 communication path
45a ejection opening
47 liquid retainer
48 forked claw
50 liquid applicator
51 cap
52 storage tank
54 liquid depressurizing mechanism (liquid depressurizing means)
55 action converter
56 outer sleeve cap
57 inner sleeve member
58 elastic structure
58a projection
59 elastic structure
59a projection
60 flange portion
61 meshing portion
R clockwise direction (pressurizing direction)

BEST MODE FOR CARRYING OUT THE INVENTION

Referring the accompanying drawings, the present invention will be detailed based on the best mode of a liquid applicator. However, the liquid applicator of the present invention should not be limited to the following embodiments.

FIG. 1 is a sectional side view showing the first embodiment of a liquid applicator.

FIGS. 2(a), 2(b) and 2(c) are a sectional side view of the structure of the front barrel portion of the first embodiment of a liquid applicator, its half-sectional, plan view and its view observed in the axial direction from the front end, respectively.

Figure 3A:
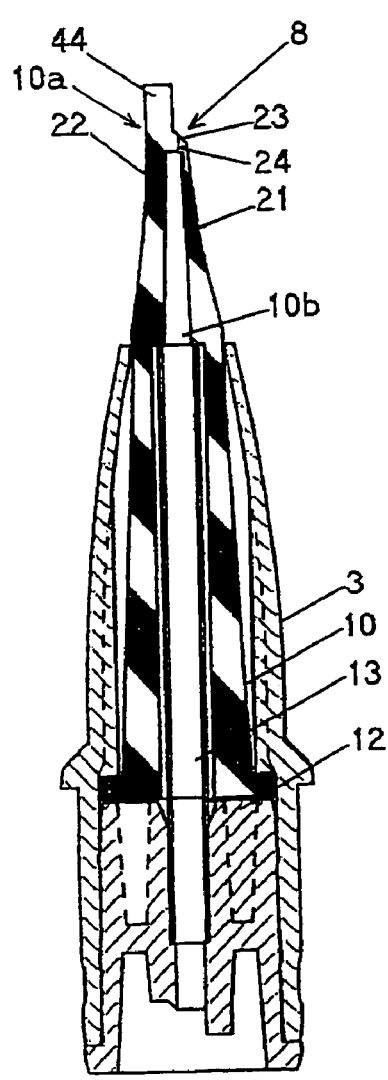
FIGS. 3(a), 3(b) and 3(c) are a sectional side view of the structure of the front barrel portion of the second embodiment of a liquid applicator, its half-sectional, plan view and its view observed in the axial direction from the front end, respectively.
Figure 3B:
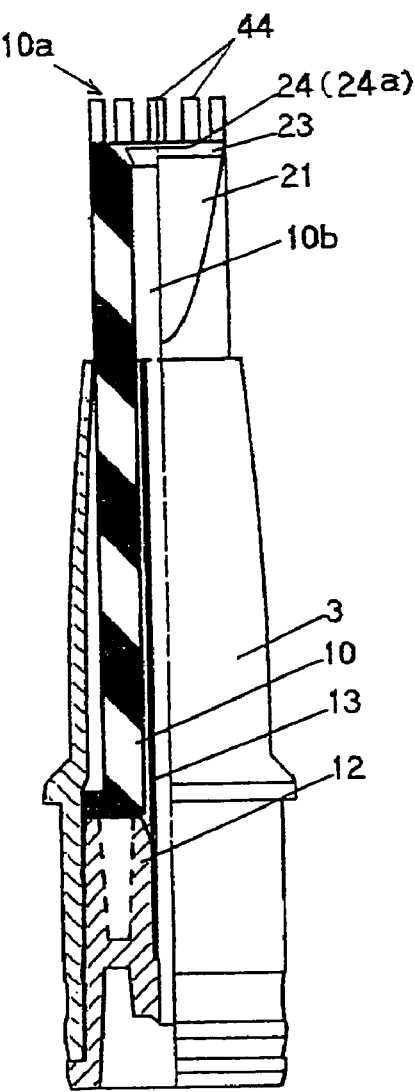
Figure 3C:
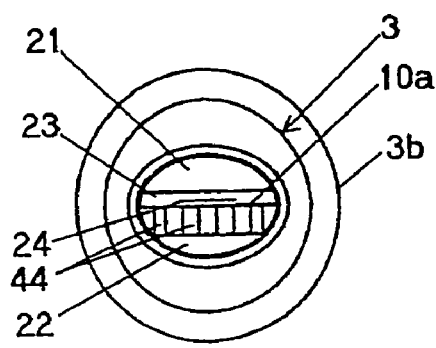

FIGS. 3(a), 3(b) and 3(c) are a sectional side view of the structure of the front barrel portion of the second embodiment of a liquid applicator, its half-sectional, plan view and its view observed in the axial direction from the front end, respectively.

Figure 4A:
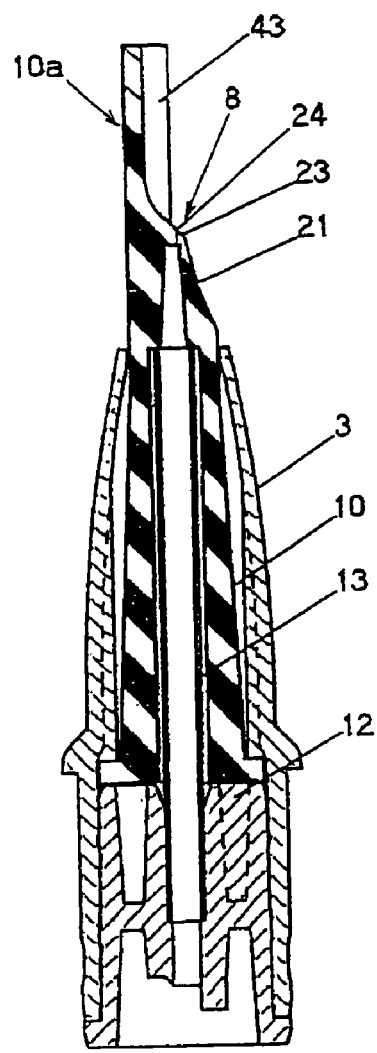
FIGS. 4(a), 4(b) and 4(c) are a sectional side view of the structure of the front barrel portion of the third embodiment of a liquid applicator, its half-sectional, plan view and its view observed in the axial direction from the front end, respectively.
Figure 4B:
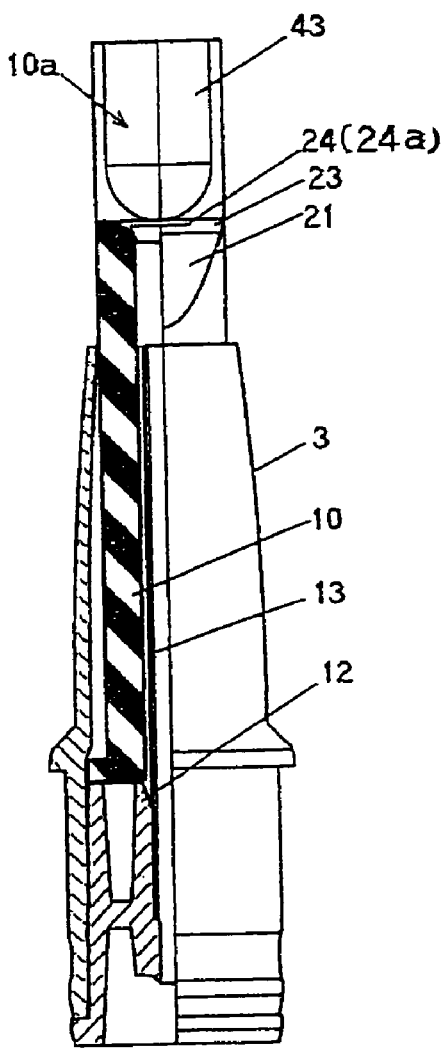
Figure 4C:
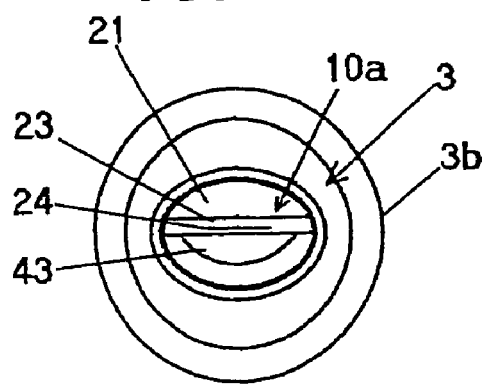

FIGS. 4(a), 4(b) and 4(c) are a sectional side view of the structure of the front barrel portion of the third embodiment of a liquid applicator, its half-sectional, plan view and its view observed in the axial direction from the front end, respectively.

Figure 5A:
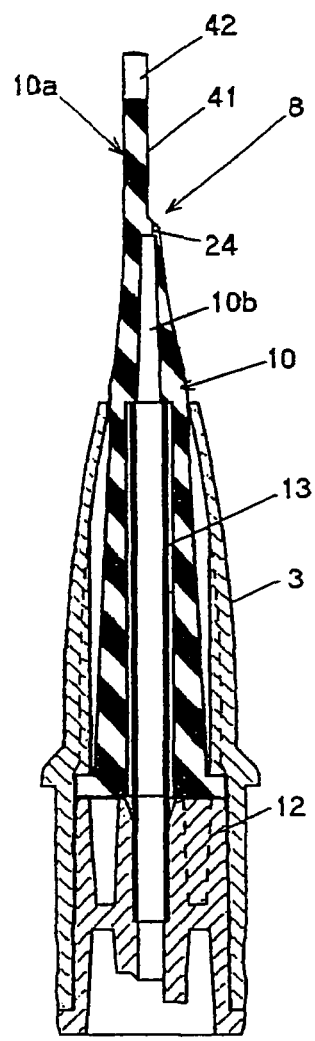
FIGS. 5(a), 5(b) and 5(c) are a sectional side view of the structure of the front barrel portion of the fourth embodiment of a liquid applicator, its half-sectional, plan view and its view observed in the axial direction from the front end, respectively.
Figure 5B:
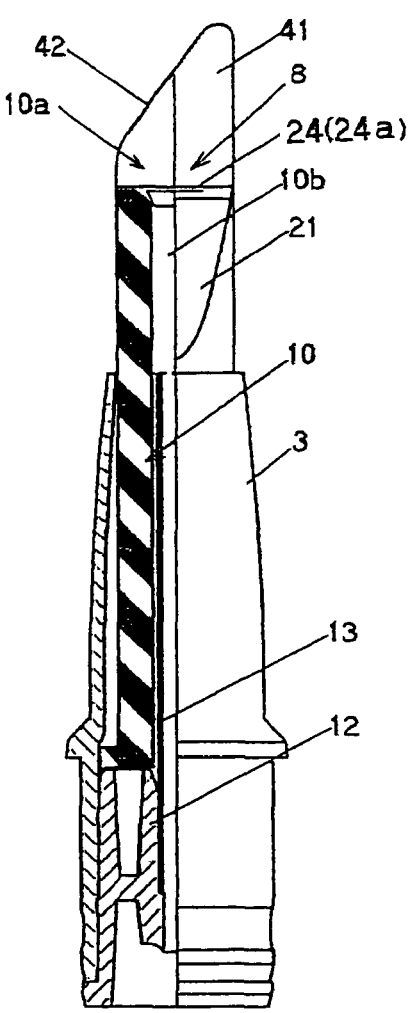
Figure 5C:
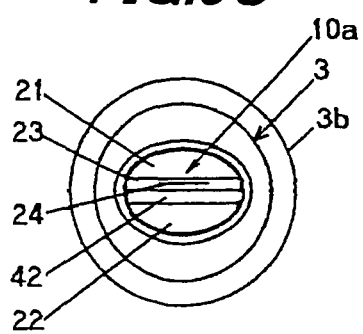

FIGS. 5(a), 5(b) and 5(c) are a sectional side view of the structure of the front barrel portion of the fourth embodiment of a liquid applicator, its half-sectional, plan view and its view observed in the axial direction from the front end, respectively.

Figure 6A:
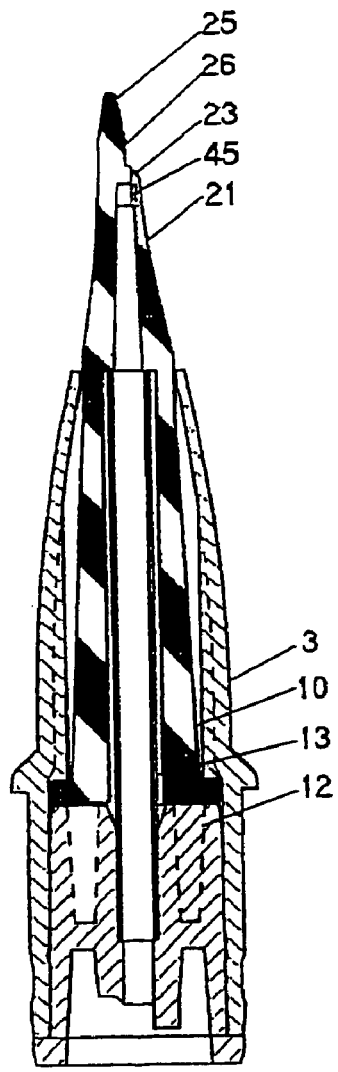
FIGS. 6(a), 6(b) and 6(c) are a sectional side view of the structure of the front barrel portion of the fifth embodiment of a liquid applicator, its half-sectional, plan view and its view observed in the axial direction from the front end, respectively.
Figure 6B:
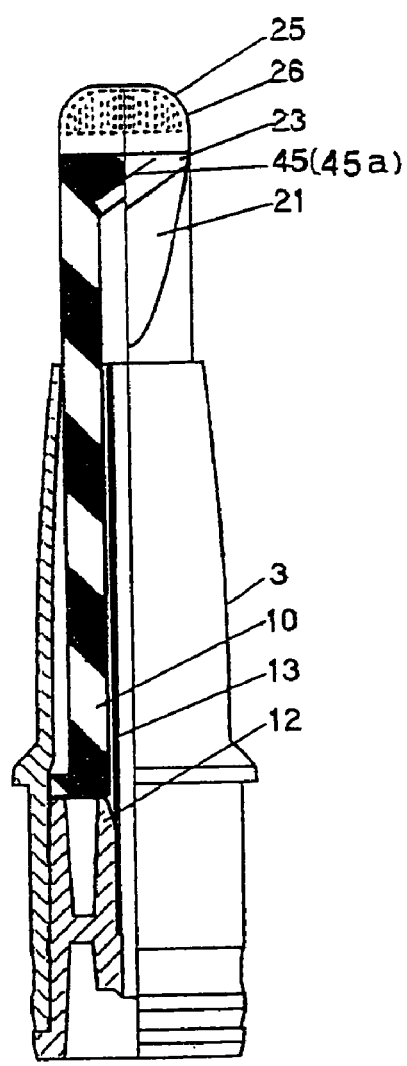
Figure 6C:
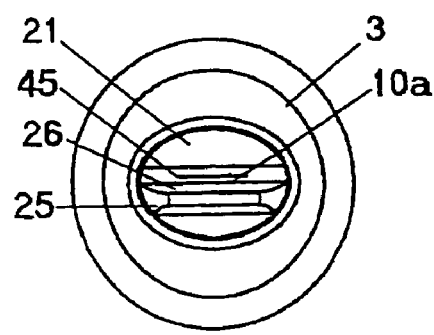

FIGS. 6(a), 6(b) and 6(c) are a sectional side view of the structure of the front barrel portion of the fifth embodiment of a liquid applicator, its half-sectional, plan view and its view observed in the axial direction from the front end, respectively.

Figures 7A, 7B:
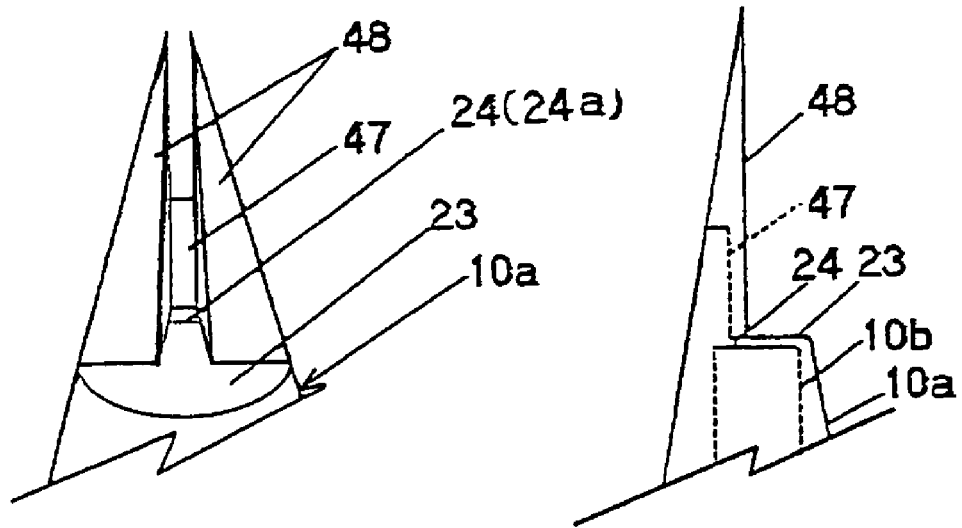
FIGS. 7(a) and 7(b) are side and plan views showing a configuration of an applying part according to the sixth embodiment of a liquid applicator, respectively.

FIGS. 7(a) and 7(b) are side and plan views showing a configuration of an applying part according to the sixth embodiment of a liquid applicator, respectively.

Figure 8:
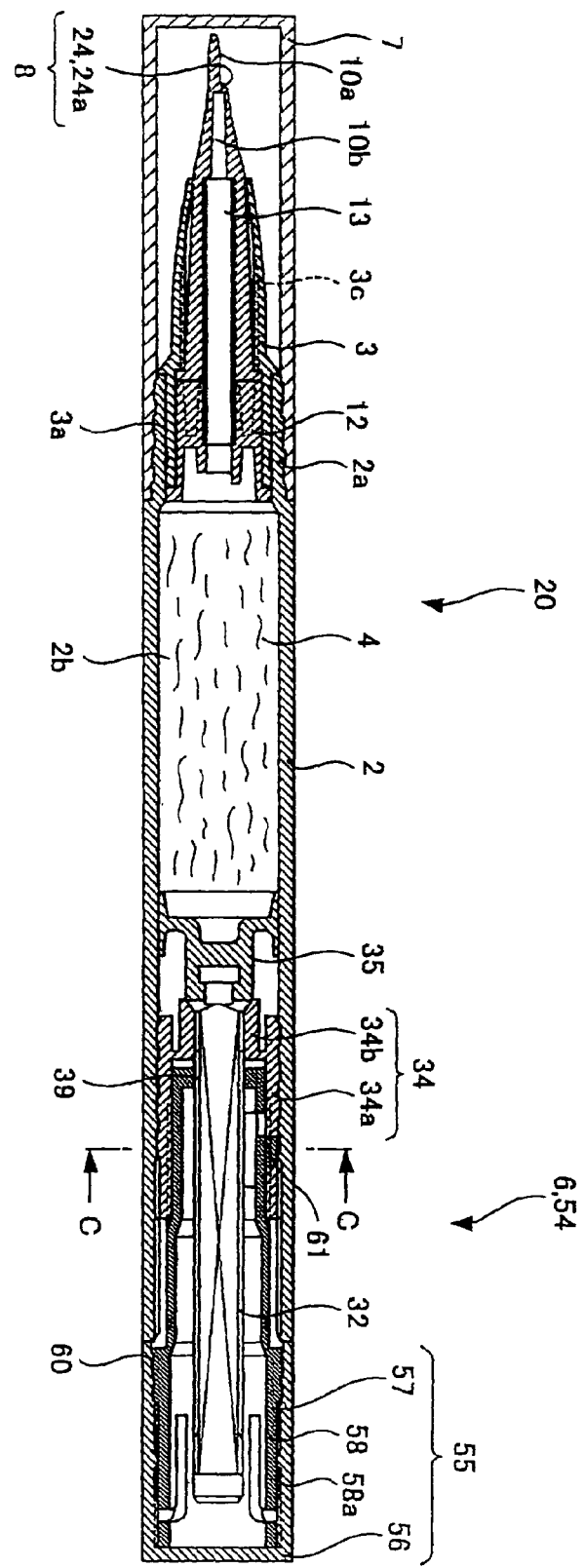
FIG. 8 is a vertical sectional view showing the seventh embodiment of a liquid applicator.

FIG. 8 is a vertical sectional view showing the seventh embodiment of a liquid applicator.

Figure 9A:
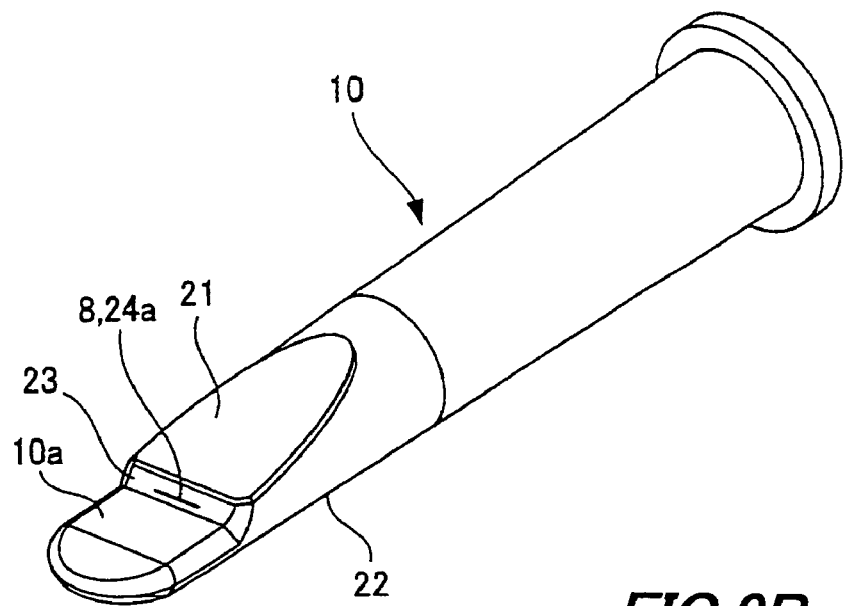
FIGS. 9(a) and 9(b) are a perspective view of an applying part according the seventh embodiment of a liquid applicator and its vertical section with cross-sections.
Figure 9B:
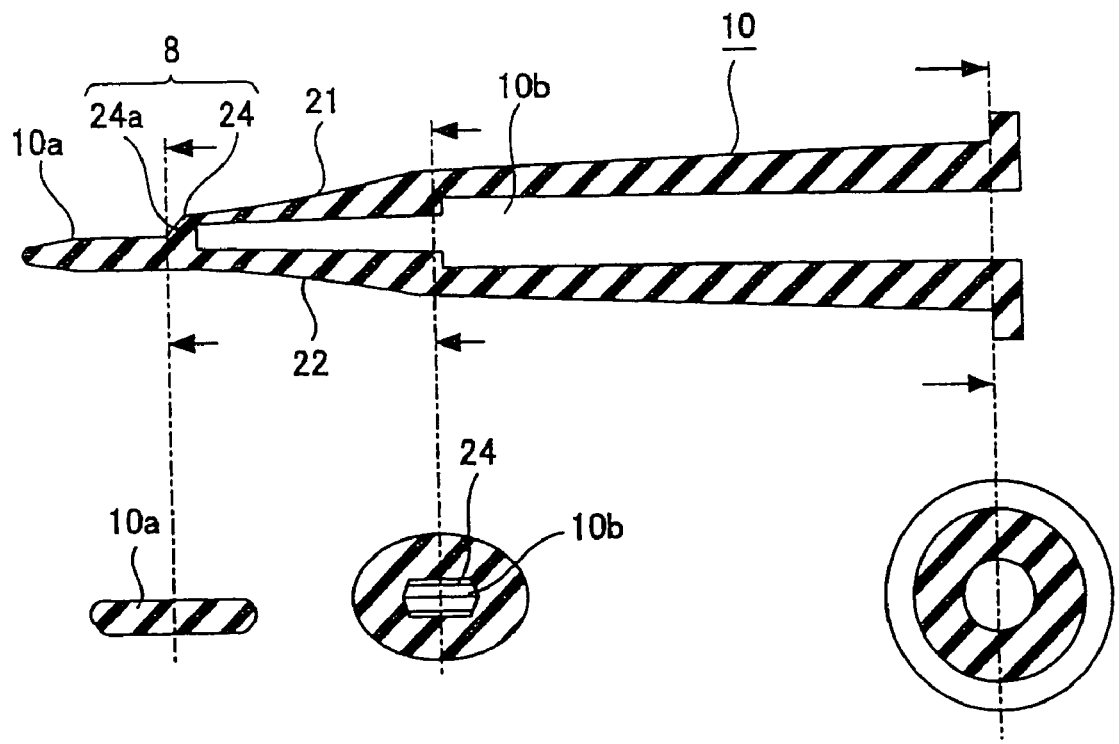

FIGS. 9(a) and 9(b) are a perspective view of an applying part according the seventh embodiment of a liquid applicator and its vertical section illustrated with cross-sections.

Figure 10A:
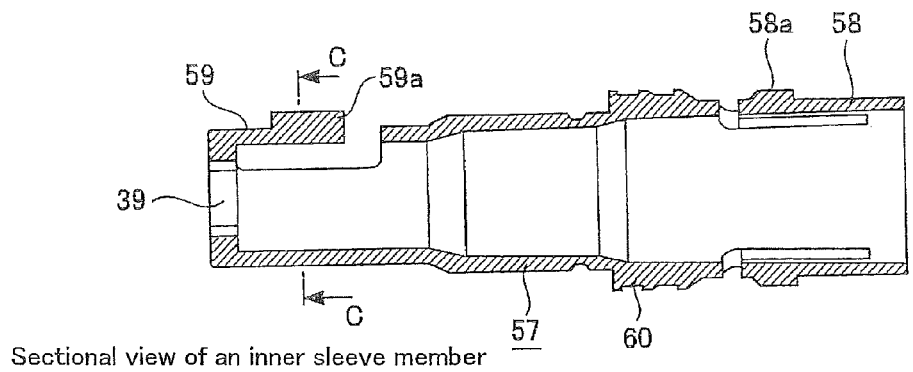
FIGS. 10(a), 10(b) and 10(c) are a vertical sectional view of an inner sleeve member for a rotary actuator according the seventh embodiment of a liquid applicator, its perspective view and a cross-sectional view cut along a line C-C in FIG. 8, respectively.
Figure 10B:
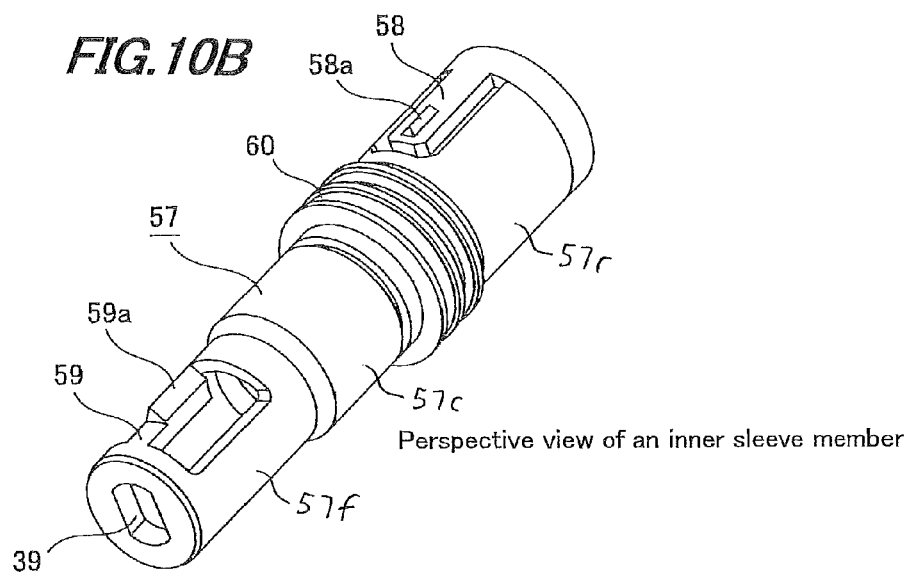
Figure 10C:
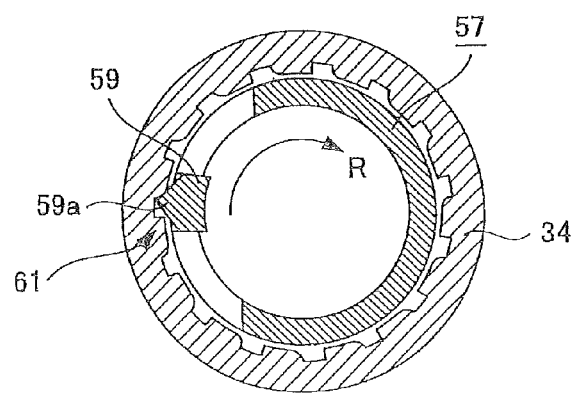

FIGS. 10(a), 10(b) and 10(c) are a vertical sectional view of an inner sleeve member for a rotary actuator according the seventh embodiment of a liquid applicator, its perspective view and a cross-sectional view cut along a line C-C in FIG. 8, respectively.

Figure 11:
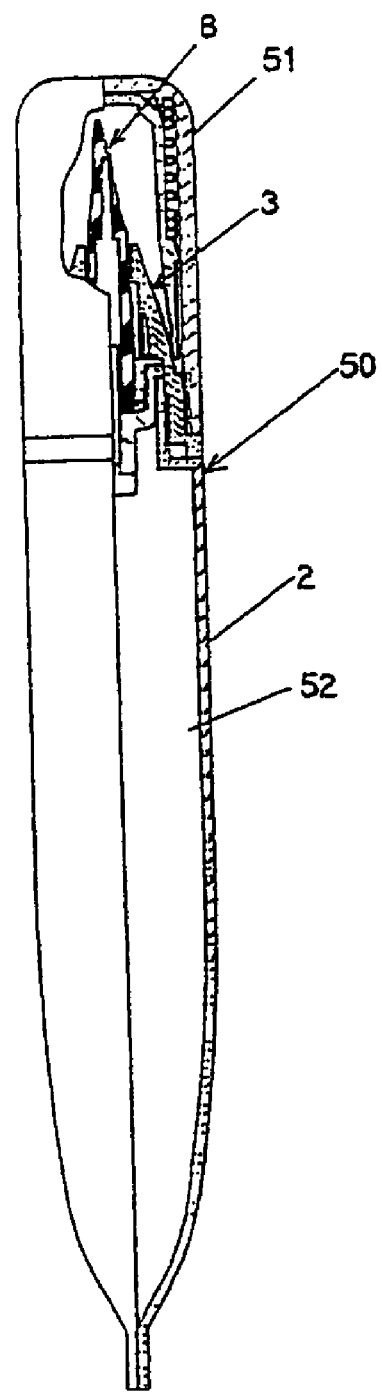
FIG. 11 is a partial sectional view showing a liquid applicator having a liquid pressing mechanism according to the eighth embodiment.

FIG. 11 is a partial sectional view of a liquid applicator having a liquid pressing mechanism according to the eighth embodiment of a liquid applicator.

As shown in FIGS. 1 and 2, a liquid applicator 1 according to the first embodiment has a liquid pressing mechanism (liquid pressing means) 6 for pressurizing an application liquid 4 inside a main body 2 so as to supply application liquid 4 to an applying member 10 by the pressing of liquid pressing mechanism 6.

Applying member 10 of liquid applicator 1 is made of an elastic body. Applying member 10 is made of an elastic material and the applying member 10 includes: a valve structure 8 which is formed with a communication path 24 for communication between the inside and outside of main body 2 and can close the communication path 24 by elasticity in the normal condition (in a state where the application liquid is not pressurized) and open communication path 24 by elastic deformation of the communication path when application liquid 4 is pressurized by liquid pressing means 6, and the applying portion 10a of applying member 10 is formed projected further forward from an ejection opening 24a of communication path 24 of valve structure 8.

Also, as shown in FIG. 1, liquid applicator 1 includes, as essential parts, main body 2 as the outer sleeve, a front barrel 3, application liquid 4, liquid pressing mechanism 6, a cap 7 and valve structure 8.

Main body 2 has a roughly tubular hollow configuration with its front end formed with a small-diametric portion 2a having an outside diameter approximately equal to the inside diameter of tapering cap 7. Cap 7 is detachably fitted to the small-diametric portion 2a.

A proximal end of front barrel 3 is fluid-tightly fitted inside the bore of small-diametric portion 2a of main body 2 while liquid pressing mechanism 6 is arranged at the rear end of main body 2 so that a piston element (gasket) 35 of liquid pressing mechanism 6 is arranged hermetically so as to move slidably along the inner wall of the bore in the rear end of main body 2.

Accordingly, the portion enclosed by the main body 2 interior, the rear end of front barrel 3 and piston element 35 constitutes an application liquid storing space (storage tank) 2b.

Liquid pressing mechanism 6 is composed of, as essential parts, a rotary actuator 31, a threaded rod 32 (pusher) and a holder 34 for threaded rod 32 and the aforementioned piston element 35.

Rotary actuator 31 is formed of an outer sleeve cap 36 and an inner sleeve member 37, being joined to each other in an unrotatable manner, and the rotatable actuator 31 as a whole is arranged rotatably in main body 2.

Holder 34 is an annular part and is unrotatably attached to main body 2. Formed in the meshing portion 38 between holder 34 and rotary actuator 31 (the outer peripheral surface at the front part of inner sleeve member 37) is a ratchet, so that rotary actuator 31 is restrained in its rotation, or is permitted to rotate in one direction only with respect to holder 34 (main body 2 fixed to it). In addition to this, it is also possible to provide a torque limiter function which permits rotation releasing its constraint when a rotational force beyond a fixed level acts in the one direction.

A male thread is formed on the outer periphery of threaded rod 32 and is mated into a female thread formed in the center bore of holder 34. The outer peripheral part of threaded rod 32 has an anomaly cam shape when viewed cross-sectionally (e.g., having an approximately oval shape by forming cutouts at both sides with respect to the diameter, when viewed cross-sectionally) while as an engaging portion 39 (at a further front part of meshing portion 38) on inner sleeve member 37 of rotary actuator 31, an anomaly cam shape corresponding to the outer peripheral shape of threaded rod 32 is formed on its center bore. The aforementioned threaded rod 32 is inserted to pass through the center bore of engaging portion 39, whereby threaded rod 32 is engaged with rotary actuator 31 (by way of engaging portion 39) so as to be able to slide in the axial direction in a relatively unrotatable manner.

Piston element 35 is connected to the front end of threaded rod 32. As rotary actuator 31 turns in the predetermined direction, threaded rod 32 advances by the means of holder 34 toward the front end of main body 2, whereby piston element 35 moves forwards and presses application liquid 4.

As shown in FIG. 2, front barrel 3 has a tapering tubular structure which is reduced in diameter as it goes toward the front end, and holds applying member 10 in its interior space that is formed from its front to rear, with the front end of the applying member sticking out. This front barrel is fixed to main body 2 as it holds the applying member. As will be described later, applying member 10 has a shape which becomes narrower and flatter as it goes to the front.

An annular fitting recess 3a is formed around the outer periphery in the rear end of front barrel 3. Fitting recess 3a is press fitted with an annular fitting projection (not shown) formed on the inner surface of small-diametric portion 2a of main body 2 so as to prevent front barrel 3 from coming off main body 2.

Formed also on the outer periphery of front barrel 3 is a flange 3b, which abuts the front end face of small-diametric portion 2a. A plurality of ribs 3c extending in the axial direction are formed equi-distantly on the inner peripheral surface of front barrel 3. The rear end faces of these ribs 3c and the front end face of a pipe joint 12 sandwich the flanged portion that is enlarged in diameter at the rear part of applying member 10 so as to hold and fix applying member 10 inside front barrel 3.

Applying member 10 is formed of an elastic member and is supported by pipe joint 12 and an application liquid feed pipe 13. Application liquid feed pipe 13 is inserted and fixed in a passage hole 12a at the center of pipe joint 12 and is inserted into a bore 10b provided for applying member 10a, from its rear end up to the middle part (front end of front barrel 3) where the bore is enlarged in diameter, to also serve as a liquid leakage preventing structure.

Applying member 10 has a flat tapering structure with tapered portions 21 and 22 formed on both sides thereof. The upper tapered portion 21 is formed with a step, where a valve structure 8 is formed at its shoulder 23. Applying portion 10a of applying member 10 is formed further frontward from valve structure 8.

Valve structure 8 has a simple structure making use of communication path 24 formed like a slit at shoulder 23 and the elastic deformation of applying portion 10a. Communication path 24 is connected to bore 10b of applying member 10 an disclosed by its elasticity in the normal condition so that application liquid 4 will not flow out. On the other hand, when application liquid 4 is pressurized by liquid pressing mechanism 6, it opens by virtue of elastic deformation.

In the present invention, applying member 10 may be totally formed of elastic material or only applying portion 10a may be formed of elastic material. As a material for applying portion 10a, elastic materials such as rubber, elastomer etc., can be mentioned as long as it is an elastic material. Further, as a material for applying portion 10a, any elastic material without continuous foam can be used without problems as long as it presents fluid-tightness. For example:
(1) Examples of rubber include NBR, silicone rubber, EPDM, fluoro silicone rubber, fluororubber, urethane rubber, natural rubber, chloroprene rubber, butadiene rubber, butyl rubber and the like.
(2) Examples of elastomer include styrene elastomer, vinyl chloride elastomer, olefin elastomer, polyester elastomer, polyamide elastomer, urethane elastomer and the like.
(3) Examples of closed cellular materials include polyethylene foam, vinyl chloride foam, polystyrene foam and the like.

As shown in FIG. 2, applying portion 10a is a part that is extended from shoulder 23 formed as a step and is formed as a flat portion 25, which is formed with a roughened surface portion 26. Application liquid 4 ejected from ejection opening 24a of communication path 24 is temporarily retained on roughened surface portion 26 of flat portion 25. The retained amount of the application liquid on it depends on the type of the cosmetic used.

In the thus configured liquid applicator 1, in the normal condition the interior of main body 2, the interior of pipe joint 12 of front barrel 3, the interior of application liquid feed pipe 13 and bore 10b of applying member 10 are filled with application liquid 4. The charged application liquid 4 will not be in contact with the external air because communication path 24 is in a closed state. Upon usage, rotary actuator 31 of liquid pressing mechanism 6 is turned. As rotary actuator 31 is rotated, threaded rod 32 advances to the front end by drive transmission through engaging portion 39. This causes piston element 35 to move forwards and pressurize application liquid 4. As application liquid 4 is pressurized, communication path 24 of valve structure 8 is opened opposing the elastic force. This causes a predetermined amount of application liquid 4 to be ejected so that the pressure of application liquid 4 is reduced approximately to atmospheric pressure and hence communication path 24 is closed.

The ejected application liquid 4, though some part may run out, is temporarily retained over roughened surface portion 26 of flat portion 25 that extends to the front end, and lead and applied to the soft applied surface such as skin etc. After the end of application, the application liquid puddled on flat portion 25 can be easily wiped by tissue, rag or the like.

In addition, since liquid pressing mechanism 6 uses a ratchet, rotary actuator 31 will rotate a predetermined amount by only a single action of rotary actuator 31, so the mechanism has the function of pushing out piston element 35 by a predetermined distance every actuation. Accordingly, it is possible to exactly dispense a desired amount of application liquid to applying portion 10a, in combination with valve structure 8 of which the functionality of the elastic material and the tightness of communication path 24 are adjusted appropriately.

Accordingly, when the applicator is not in use, valve structure 8 takes the normal state, so that bacteria and other germs are prevented from invading. On the other hand, upon being pressurized, communication path 24 that has been closed elastically deforms and opens its ejection opening 24a, through which application liquid 4 is dispensed for smooth usage.

Further, since flat portion (liquid retainer) 25 for temporarily holding the ejected application liquid 4 is formed in applying portion 10a near ejection opening 24a of communication path 24, it is possible to prevent the application liquid 4 from dripping even if application liquid 4 abruptly rushes out.

As understood from the above, the application liquid 4 that comes in contact with the external air after usage is limited to that residing in applying portion 10a from ejection opening 24a, which can be easily removed. As a result, it is not only possible to apply application liquid 4 even though it is high in viscosity, but also fully protect the stored application liquid 4 against the contamination by microbes and the like from the external air and outside environment.

FIG. 3 is a view showing an applying part according to the second embodiment of a liquid applicator according to the present invention. Since the liquid applicator shown in FIG. 3 has almost the same structure as that of the front barrel shown in FIG. 2 except for its applying member 10, the same and similar components are allotted with like reference numerals and their detailed description is omitted.

As shown in FIG. 3, a comb portion 44 is formed further forwards from ejection opening 24a of communication path 24 located at shoulder 23 of applying member 10. The application liquid 4 ejected from ejection opening 24a temporarily adheres to comb portion 44 or is retained by surface tension of the liquid or the like. That is, comb portion 44 functions as a liquid retainer for temporal retention and also plays a central role of applying portion 10a.

FIG. 4 is a view showing an applying part according to the third embodiment of a liquid applicator according to the present invention.

Since the liquid applicator shown in FIG. 4 has almost the same structure as that of the front barrel shown in FIG. 2 except for its applying member 10, the same and similar components are allotted with like reference numerals and their detailed description is omitted.

As shown in FIG. 4, a roughly shovel-like portion 44 such as a shovel, spade or the like is formed further forwards from ejection opening 24a of communication path 24 located at shoulder 23 of applying member 10. The application liquid 4 ejected from ejection opening 24a is temporarily held. That is, roughly shovel-like portion 44 functions as a temporal retainer of liquid and also plays a central role of applying portion 10a.

FIG. 5 is a view showing an applying part according to the fourth embodiment of a liquid applicator according to the present invention.

Since the liquid applicator shown in FIG. 5 has almost the same structure as that of the front barrel shown in FIG. 2 except for its applying member 10, the same and similar components are allotted with like reference numerals and their detailed description is omitted.

As shown in FIG. 5, a temporal liquid retainer 41 that is extended further forwards from ejection opening 24a of communication path 24 located at shoulder 23 of applying member 10 is formed in a knife-like form having an acute portion 42 at its front end. With this shape, it is possible to apply application liquid 4 exactly along the contours of the eyes and lips while temporarily holding the liquid.

FIG. 6 is a view showing an applying part according to the fifth embodiment of a liquid applicator according to the present invention.

Since the liquid applicator shown in FIG. 6 has almost the same structure as that of the front barrel shown in FIG. 2 except for its applying member 10, the same and similar components are allotted with like reference numerals and their detailed description is omitted.

As shown in FIG. 6, in applying member 10, an ejection opening 45a of communication path 45 is formed obliquely with respect to the axial direction of applying member 10. Thus, in the present invention, the way of forming a slit for ejection opening 45a of communication path 45 can be changed as appropriate depending on the configuration of the applying part and the applied surface.

FIG. 7 is a view showing an applying part according to the sixth embodiment of a liquid applicator according to the present invention.

Since the liquid applicator shown in FIG. 7 has almost the same structure as that of the front barrel shown in FIG. 2 except for its applying member 10, the same and similar components are allotted with like reference numerals and their detailed description is omitted.

As shown in FIG. 7, in applying portion 10a, forked claws 48 are formed on both sides of a liquid retainer 47 that is extended further forwards from ejection opening 24a of communication path 24 located at its shoulder 23. This configuration facilitates the application liquid to be retained between the claws by its surface tension and also enables preferable application over special applied surfaces.

FIG. 8 is a vertical sectional view showing the entire body of the seventh embodiment of a liquid applicator of the present invention; FIG. 9 is a detailed illustration of its applying member; and FIG. 10 is a detailed illustration of a rotary actuator.

Since a liquid applicator 20 of the seventh embodiment shown in FIG. 8 has almost the same structure as that in the first embodiment of a liquid applicator of the present invention shown in FIGS. 1 and 2 except for the structure of its liquid depressurizing mechanism (liquid depressurizing means) 54, the same and similar components are allotted with like reference numerals and their detailed description is omitted.

As shown in FIG. 8, liquid applicator 20 according to the seventh embodiment has liquid depressurizing mechanism 54 for depressurizing application liquid 4 inside main body 2. Valve structure 8 is configured so that after liquid pressing mechanism 6 stops pressurizing application liquid 4, the valve structure can forcibly return the elastic deformation of communication path 24 to the normal condition by reducing the pressure on application liquid 4 by means of the liquid depressurizing mechanism 54 and thereby close the communication path 24.

Liquid pressing mechanism 6 and liquid depressurizing mechanism 54 comprise: a piston element (pressure applicator) 35 which moves forwards and backwards in application liquid storage space 2b inside main body 2 to pressurize and depressurize application liquid 4; and an action converter 55 for converting the user's rotational control over rotary actuator 31 which fronts on the outside of main body 2, into the aforementioned forward and backward movement of piston element 35.

Specifically, as shown in FIGS. 8 to 10, liquid applicator 20 according to the seventh embodiment is composed of, as essential components, main body 2 as the outer sleeve, front barrel 3, application liquid 4, liquid pressing mechanism 6, liquid depressurizing mechanism 54, action converter 55, cap 7 and valve structure 8, and differs in the configurations of liquid depressurizing mechanism 54 and action converter 55, from liquid applicator 1 including liquid pressing mechanism 6 only, of the first embodiment shown in FIG. 1.

Applying member 10 employs one shown in FIG. 9 having the same configuration shown in FIG. 2. That is, applying member 10 has a flat tapering front end, projected and exposed from the front end of front barrel 3, and having tapered portions 21 and 22 formed on both sides thereof, as perceptively shown in FIG. 9(a) and sectionally shown with different sections in FIG. 9(b). The upper tapered portion 21 is formed with a step, where valve structure 8 of slit-like communication path 24 connected to the front end of bore 10b is formed at its shoulder 23. Applying portion 10a of applying member 10 is formed further forwards from valve structure 8. It goes without saying that as applying member 10, those shown in FIGS. 3 to 7 can be adopted instead of ones shown in FIGS. 2 and 9.

As shown in FIG. 8, in the above-described liquid applicator 20 according to the seventh embodiment the integration of liquid pressing mechanism 6 and liquid depressurizing mechanism 54 is arranged in the rear end of main body 2, and a piston element 35 of liquid pressing mechanism 6 and liquid depressurizing mechanism 54 is arranged hermetically so as to move slidably along the inner wall of the bore in the rear end of main body 2.

The liquid pressing mechanism 6 and liquid depressurizing mechanism 54 include, as essential components, action converter 55, threaded rod 32 (pusher) and holder 34 for threaded rod 32 and the aforementioned piston element 35.

Action converter 55 is composed of an outer sleeve cap 56 and inner sleeve member (also called "advancing member") 57, which are joined so as not to be rotatable relative to each other in the usual condition and so as to rotate relative to each other by a rotational force equal to or greater than a fixed level, and the entire action converter 55 is arranged so as to be rotatable with respect to main body 2.

Detailedly, as shown in FIG. 10, inner sleeve member 57 has an approximately cylindrical form having different diameters becoming greater stepwise from its front part through center part to rear part, with cutouts formed at different positions.

Formed in inner sleeve member 57 are a cantilevered elastic structure 58, defined by a U-shaped cutout formed on the side surface portion in the rear part, and at least, producing elasticity radially outwardly, and another cantilevered elastic structure 59, defined by a U-shaped cutout formed on the side view in the front part, and at least, producing elasticity radially outwardly.

These cantilevered elastic structures 58 and 59 have gabled roof-like projections 58a and 59a having a triangular cross-section when viewed in the axial direction, respectively, on their surfaces so that they project radially outwardly.

Formed at a position close to the center part in the rear part of inner sleeve member 57 is a flange portion 60 which is greater stepwise in diameter than the center part and has a multiple number of annular projections. The front end face of this flange portion 60 abuts the rear end face of main body 2 when the front part of inner sleeve member 57 is fitted into main body 2, so that the sleeve will not slide into main body 2 any further. When outer sleeve cap 56 has been fitted over the rear part of inner sleeve member 57, a stepped portion on the inner periphery of outer sleeve cap 56 fits on the aforementioned outer periphery of flange portion 60 in a rotatable manner so as to prevent the cap from coming off.

Formed in the rear part on the inner peripheral surface of outer sleeve cap 56 is a groove extending in the axial direction. The projection 58a on the aforementioned cantilevered elastic structure 58 surface becomes engaged in this groove, forming a clutch mechanism, so that inner sleeve member 57 and outer sleeve cap 56 will integrally rotate when it is operated while projection 58a of elastic structure 58 dislodges from the groove of outer sleeve cap 56 and starts relatively rotating when a rotational force equal to or greater than a fixed level is applied.

An engaging portion 39 formed in the front part of inner sleeve member 57 is a front center hole having an anomaly cam shape corresponding to the outer peripheral shape of threaded rod 32. The aforementioned threaded rod 32 is inserted through the center hole of engaging portion 39 so that threaded rod 32 is engaged with action converter 55 (via engaging portion 39) and can slide in the axial direction but cannot relatively rotate.

Also, the outer peripheral surface other than the cutouts of threaded rod 32 that is inserted through and engaged with this engaging portion 39 is formed with a male thread, which is screwed and fitted to the female thread formed inside the center bore of holder 34.

In the embodiment the male thread and female thread are threaded right-handed, and as outer sleeve cap 56 of action converter 55 is turned clockwise with respect to main body 2, threaded rod 32 is rotated clockwise via engaging portion 39, whereby the male thread of threaded rod 32 is moved forwards by the female thread of holder 34 and pushes piston element 35, which in turn pressurizes the application liquid inside application liquid storing space (storage tank) 2b (liquid pressing function). Conversely, when the aforementioned outer sleeve cap 56 is rotated counterclockwise with respect to main body 2, threaded rod 32 is rotated counterclockwise via engaging portion 39, whereby the male thread of threaded rod 32 is moved backwards by the female thread of holder 34 and pulls piston element 35, which in turn depressurizes the application liquid inside application liquid storing space 2b (liquid depressurizing function).

It should be noted that the screw fitting portions of threaded rod 32 and holder 34 may be threaded left-handed, if required. In this case, application liquid 4 is pressurized by a counterclockwise rotation and is depressurized by a clockwise rotation, in contrast to the above case.

This holder 34 is an annular member having a roughly two-concentric cylindrical structure in which a small-diametric portion 34b is fixed at the front inside of a large-diametric portion 34a, and is attached in an unrotatable manner with its outer peripheral surface of large-diametric portion 34a fitted inside main body 2. A right-handed female screw thread is formed on the inner peripheral surface of narrow-diametric portion 34b of holder 34 while a meshing portion 61 made up of teethed ratchet grooves into which projection 59a of the aforementioned elastic structure 59 fits is formed around the whole inner surface of large-diametric portion 34a.

Each tooth in meshing portion 61 is so formed that one of the inward corners has a gently sloping shoulder and the other has a square shoulder, as shown in FIG. 10(c). With the aforementioned inner sleeve member 57 inserted into holder 34 from behind, projection 59a of the aforementioned elastic structure 59 fits into meshing portion 61.

As action converter 55 is turned clockwise (in the direction of arrow R in FIG. 10, in one way) with respect to main body 2, inner sleeve member 57 rotates clockwise via outer sleeve cap 56 and threaded rod 32 also rotates clockwise via engaging portion 39, so that threaded rod 32 moves forwards by screw engagement with the female thread of holder 34 to advance piston element 35 and pressurize the application liquid in the main body.

Concerning the arrangement of action converter 55, threaded rod 32 and holder 34, as inner sleeve member 57 of action converter 55 is turned in one direction (in the rotational direction of R), projection 59a, while being fitted within the groove between teeth, abuts the aforementioned gently sloping shoulder and climbs over it and then falls into the next groove. Accordingly, this arrangement constitutes a pressurizing structure which allows for easy rotation with a clicking sensation. Also concerning the arrangement of action converter 55, threaded rod 32 and holder 34, as this inner sleeve member 57 is turned in the other direction (in the rotational direction opposite to R), projection 59a, while being fitted within the groove between teeth, abuts the aforementioned square shoulder and climbs over it and then falls into the next groove. Accordingly, this rotation needs a greater force (torque) than that needed by the rotation in the first direction, hence this arrangement constitutes a depressurizing structure which causes heavy load to rotate with a tight feeling.

In the above, meshing portion 61 facilitates easy rotation of holder 34 and action converter 55 (the outer peripheral surface in the front part of inner sleeve member 57) in the first direction in a ratcheting manner when application liquid 4 is wanted to be ejected. On the other hand, when application liquid 4 is pulled in after usage the device is turned in the other direction so as to close the slit of valve structure 8 by force; however this rotation is restrained and needs much effort so that application liquid 4 can be depressurized gently. With this configuration, it is possible to reliably prevent valve structure 8 at the ejection opening from closing quickly more than needed and prevent air from being suctioned as application liquid 4 is abruptly pulled into main body 2.

Needless to say, in order to prevent over quick suctioning of application liquid 4 when a rotational force equal to or greater than a fixed level acts on action converter 55 at the time of depressurizing, a torque limiter function that releases engagement between the inner peripheral surface of the aforementioned outer sleeve cap 56 and the inner sleeve member 57 with projection 58a of elastic structure 58 is provided which releases the application of torque so as to make the cap inactively rotate.

FIG. 11 is a view showing a liquid pressing mechanism liquid pressing means) according to the eighth embodiment of a liquid applicator of the present invention.

Since a liquid applicator 50 shown in FIG. 11 has almost the same structure as that of the liquid applicator 1 shown in FIG. 2, the same and similar components are allotted with like reference numerals and their detailed description is omitted.

As sown in FIG. 11, a cap 51 of liquid applicator 50 is formed of a two-layered cap so as to protect the structure of front barrel 3 in a more air-tight manner. The valve structure 8 of applying member 10 has the same structure as that of the valve structure shown in FIG. 2.

The liquid pressing mechanism shown in FIG. 11 is constituted of a flexible and resilient application liquid storage tank (application liquid storing space) 52 that forms main body 2. With this hand-powered liquid pressing mechanism, application liquid 4 is pressurized in main body 2 by lightly pushing main body 2 with the fingers, so that application liquid 4 is ejected to flat portion (temporal liquid retainer) 25 as slit-like communication path 24 is deformed. Further, since the liquid can be temporarily retained by the presence of flat portion 25, it is possible to avoid dripping of liquid even if main body 2 is more or less over-pressurized. Also, a liquid depressurizing function for depressurizing the application liquid is achieved by stopping the pressing after pressure application, so that valve structure 8 of communication path 24 can be forcibly closed.

Upon construction of the liquid pressing mechanism and valve structure 8 of this kind, the following design and setup are preferably put into practice.

1. In order to open communication path 24, the pressure applied on the application liquid by the liquid pressing mechanism preferably falls within a range that is greater than 1.0 times to 5 times or lower of the atmospheric pressure, and more preferably, falls within the range from 1.001 to 3.000 times. If the pressure exceeds the above range, there is a fear that the application liquid will abruptly rush out from communication path 24. If the pressure is less than the above range, there is a risk of liquid leakage due to poor sealing of communication path 24 if general vibration and the like is applied to liquid applicator 50 in the normal condition.

2. Though it depends on the kind of the elastic material of applying portion 10a and the condition of the applied surface, generally it is preferred that the slit width for communication path 24 falls within the range of 10 to 90% of the width of the applying portion, and particularly within the range of 20 to 80%. If the slit width exceeds the above range, there is a risk of liquid leakage due to poor sealing of communication path 24 if general vibration and the like is applied to liquid applicator 1 in the normal condition.

3. The slit length for communication path 24 is preferably equal to or greater than 0.01 mm, more preferably falls within range of 0.05 to 5.0 mm. The slit length within this range is preferable to provide the function of valve under pressure in the above-specified range. If the slit length is less than the above range, there is a risk of liquid leakage due to poor sealing of communication path 24 if general vibration and the like is applied to liquid applicator 1 in the normal condition.

4. The elastic coefficient of the elastic material used for applying member 10 preferably falls within the range from 10 to 100, particularly preferably within the range from 10 to 90. If it is less than the above range, there is a fear that communication path 24 can not be fully closed by its elastic force. If it exceeds the above range, there is a risk of application liquid 4 abruptly rushing out from the ejection opening because excessively high a pressure is needed for application liquid 4.

INDUSTRIAL APPLICABILITY

Since the liquid applicator of the present invention has a valve structure in the applying part, it is possible to prevent bacteria from entering the main body in the normal condition, hence no decay or degradation of the application liquid will occur. As a result, the present invention provides a liquid applying part which can safely apply the surface of a soft object to be applied such as skin, oral cavity, etc., hence is high in industrial applicability.

The invention claimed is:
1. A liquid applicator comprising: a main body having an application liquid storage space, an applying member having an applying portion, and a liquid pressing means for pressurizing an application liquid inside the main body so as to supply the application liquid to the applying member by the pressing of the liquid pressing means, characterized in that the applying member is made of an elastic material and includes: a valve structure which is formed with a communication path for communication between the inside and outside of the main body and can close the communication path by elasticity in a normal condition and open the communication path by elastic deformation of the communication path when the application liquid is pressurized by the liquid pressing means, the communication path of the valve structure includes an ejection opening for ejecting the application liquid onto the applying portion, the ejection opening being disposed in a shoulder formed as a step in the applying member, and the applying portion is disposed on the shoulder and extends forward from the ejection opening.

2. The liquid applicator according to claim 1, wherein the applying portion of the applying member is formed projected further forward from the ejection opening of the communication path of the valve structure.

3. The liquid applicator according to claim 2, further comprising: a liquid depressurizing means for depressurizing the application liquid inside the main body, wherein the valve structure is configured so that, after the liquid pressing means stops pressurizing the application liquid, the valve structure can forcibly return the elastic deformation of the communication path to the normal condition by reducing the pressure on the application liquid by the liquid depressurizing means and thereby close the communication path.

4. The liquid applicator according to claim 3, wherein the liquid pressing means and liquid depressurizing means comprise: a pressure applicator which moves forwards and backwards in the application liquid storage space inside the main body to pressurize and depressurize the application liquid; and an action converter for converting the user's rotational control over a rotary actuator which is rotatably arranged in the main body, into the forward and backward movement of the pressure applicator.

5. The liquid applicator according to claim 2, wherein the applying portion projected from the ejection opening of the valve structure constitutes a liquid retainer for temporarily retaining the application liquid or includes the liquid retainer.

6. The liquid applicator according to claim 5, further comprising: a liquid depressurizing means for depressurizing the application liquid inside the main body, wherein the valve structure is configured so that, after the liquid pressing means stops pressurizing the application liquid, the valve structure can forcibly return the elastic deformation of the communication path to the normal condition by reducing the pressure on the application liquid by the liquid depressurizing means and thereby close the communication path.

7. The liquid applicator according to claim 6, wherein the liquid pressing means and liquid depressurizing means comprise: a pressure applicator which moves forwards and backwards in the application liquid storage space inside the main body to pressurize and depressurize the application liquid; and an action converter for converting the user's rotational control over a rotary actuator which is rotatably arranged in the main body, into the forward and backward movement of the pressure applicator.

8. The liquid applicator according to claim 1, further comprising: a liquid depressurizing means for depressurizing the application liquid inside the main body, wherein the valve structure is configured so that, after the liquid pressing means stops pressurizing the application liquid, the valve structure can forcibly return the elastic deformation of the communication path to the normal condition by reducing the pressure on the application liquid by the liquid depressurizing means and thereby close the communication path.

9. The liquid applicator according to claim 8, wherein the liquid pressing means and liquid depressurizing means comprise: a pressure applicator which moves forwards and backwards in the application liquid storage space inside the main body to pressurize and depressurize the application liquid; and an action converter for converting the user's rotational control over a rotary actuator which is rotatably arranged in the main body, into the forward and backward movement of the pressure applicator.

10. The liquid applicator according to claim 1, wherein the material of the elastic body used for the applying member is rubber.

11. The liquid applicator according to claim 1, wherein the material of the elastic body used for the applying member is elastomer.

12. The liquid applicator according to claim 1, wherein the material of the elastic body used for the applying member is a closed cellular material having resilience.

* * * * *